though ot United States Patent [19] [11] 4,115,587
Lunsford et al. [45] Sep. 19, 1978

[54] FATTY ACID AMIDES OF NORFENFLURAMINE AND COMPOSITIONS AND METHODS THEREOF

[75] Inventors: Carl D. Lunsford, Richmond; Albert D. Cale, Jr., Mechanicsville, both of Va.

[73] Assignee: A. H. Robins Company, Inc., Richmond, Va.

[21] Appl. No.: 751,294

[22] Filed: Dec. 16, 1976

Related U.S. Application Data

[63] Continuation-in-part of Ser. No. 655,195, Feb. 4, 1976, abandoned.

[51] Int. Cl.² ...................... A61K 31/165; C09F 5/00
[52] U.S. Cl. ..................................... 424/324; 260/404
[58] Field of Search .......................... 424/324; 260/404

[56] References Cited
U.S. PATENT DOCUMENTS

| 3,590,057 | 6/1971 | Suzuki et al. | 260/404 |
| 3,597,458 | 8/1971 | Nakamura et al. | 260/404 |
| 3,621,043 | 11/1971 | Seki | 424/324 X |
| 3,728,459 | 4/1973 | Seki | 424/324 X |
| 3,741,999 | 6/1973 | Seki | 260/404 |
| 3,759,979 | 9/1973 | Beregi et al. | 424/324 |
| 3,944,675 | 3/1976 | Synchowicz et al. | 260/404 |
| 3,995,059 | 11/1976 | Fukumaru et al. | 260/404 |

OTHER PUBLICATIONS

Chem. Abs., 1968, p. 87027q, vol. 68.
Chem. Abs., 1968, vol. 68, p. 28343s.
Chem. Abs., 1969, vol. 70, p. 104898n.
Chem. Abs., 1969, vol. 71, p. 79708j.

Primary Examiner—Dale R. Ore

[57] ABSTRACT

Novel amides of norfenfluramine having the formula

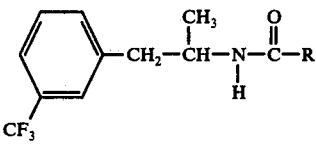

wherein R is selected from the group consisting of alkyl and alkenyl radicals having 12 to 22 carbon atoms and compositions and methods for combating atherosclerosis and hypercholesteremia, with beneficial side effects useful for combating obesity in atherosclerotic subjects are disclosed. The compounds lower lipid values and simultaneously inhibit appetite and reduce weight gain from ingested food with minimal side effects.

21 Claims, No Drawings

FATTY ACID AMIDES OF NORFENFLURAMINE AND COMPOSITIONS AND METHODS THEREOF

BACKGROUND OF THE INVENTION

This application is a continuation-in-part of application Ser. No. 655,195 filed Feb. 4, 1976 now abandoned.

The present invention relates to novel fatty acid amides or norfenfluramine which are cholesterol-lowering agents having beneficial side effects. More particularly, the invention is concerned with the long chain fatty acid amides of norfenfluramine which have dual action in reducing elevated cholesterol levels in mammalian subjects on a high cholesterol diet by interfering with cholesterol absorption and cholesterol synthesis in the liver and complementary activity in reducing weight gain, said reduction in weight gain due in part to reduced appetite and in part to lowered feed efficiency of ingested food. The cholesterol-lowering agents of this invention are ideally suited for combating diseases of atherosclerosis and hypercholesteremia in mammalian subjects without objectionable side effects and combating obesity in subjects afflicted with said diseases.

Atherosclerosis, a form of arteriosclerosis characterized by clogging of blood vessels, is due in part from deposition of excess lipids from the blood stream, primarily cholesterol and triglycerides which circulate through the body conjugated with proteins as lipoproteins, cholesterol appearing to be the larger threat. Decreasing the concentration of lipids in the blood appears to be a desirable means of combating atherosclerosis and heart disease associated therewith. Lipid values in the blood may be reduced by each or a combination of several methods depending upon the primary type of hyperlipemia-limiting lipid intake by selection of foods, by voluntary dietary restriction of food generally, by administration of anorectic drugs which limit food intake generally, or by use of drugs known as antihyperlipidemic agents. In the use of an antihyperlipidemic agent, it may be generalized that no one drug is completely effective in lowering all classes of serum lipids, and no one drug is equally effective in lowering cholesterol and triglycerides. Consequently, there is need for more effective drugs in combating atherosclerosis.

Anti-hyperlipidemic agents are believed to function in one or more ways to lower serum cholesterol as follows:

(1) Inhibition of synthesis of cholesterol in the liver and/or in the ileum;
(2) Inhibition of absorption of dietary cholesterol;
(3) Promotion of excretion by increased catabolism of cholesterol from the circulating lipids and from extra hepatic tissue.

The association of atherosclerosis with high serum cholesterol levels has directed the treatment of this disease to agents which lower serum cholesterol. Cholestyramine, which is polystyrene trimethylbenzylammonium chloride, and clofibrate, which is ethyl p-chlorophenoxyisobutyrate, act selectively to reduce cholesterol primarily by interfering with its alimentary absorption and synthesis respectively.

Other prior art compounds which are long chain fatty acid amides of certain α-methylbenzylamines and anilines having cholesterol-lowering activity ascribed thereto are disclosed in U.S. Pat. Nos. 3,621,043 and 3,728,459, α-methylbenzyl linoleamide being of particular interest.

Obesity is often closely associated with atherosclerosis and may be caused by the same root anomaly in the chemistry of individual mammalian subjects.

The present invention is based on the unexpected findings that certain fatty acid amides of norfenfluramine act to reduce cholesterol not only by lowering its absorption but its synthesis as well and that feed efficiency as well as appetite are both lowered to effect reduction in weight gain.

Thus the compounds of the present invention have multiple functions in controlling lipid values in mammalian blood serum as follows:

(1) Appetite inhibition which lowers cholesterol intake;
(2) Lowering of cholesterol absorption; and
(3) Lowering of cholesterol synthesis in the liver.

One of these functions, (3) the lowering of cholesterol synthesis in the liver, is not characteristic of the prior art, α-methylbenzylamides, and function (2) the lowering of liver and serum cholesterol, is more pronounced in the compounds of the present invention in the hypercholesteremic diet. In addition, the compounds differ from prior art amide compounds in that the amides of the present invention reduce weight gain dually in two ways, i.e., by (1) reducing appetite, and (2) reducing feed efficiency. While it has been stated in U.S. Pat. No. 3,621,043 that the prior art compounds do not affect the appetite, it was reported in the Journal of Atherosclerosis Research, Vol. 9, pages 65–71 (1969) that one prior art compound, α-methylbenzyl linoleamide, did suppress gain in body weight of rats which seemed to be caused by reduced feed intake. As set forth hereinbelow, it will be seen that in addition to suppressing appetite the compounds of the present invention reduce feed efficiency, a function not seen with prior art compounds studied.

A further distinction over the said prior art amides is greater reduction in low-density lipid carriers in blood serum. A reduction with decrement in high density lipid carriers with increasing concentration using compounds of the present invention was observed.

The compounds of the present invention are, therefore, more suitable for controlling lipid values in blood serum and have beneficial side effects in controlling obesity not attributable to said prior art amide compounds.

SUMMARY OF THE INVENTION

The present invention provides novel amides of norfenfluramine and compositions and methods for lowering elevated serum cholesterol levels in mammalian subjects fed an hypercholesteremic diet. The compounds act in multiplicity of ways of lower serum liver cholesterol and are ideally suited for combating atherosclerosis in subjects suffering therefrom. In addition, the compounds retain some of the anorectic activity of the parent amine, norfenfluramine, without any of the undesirable side effects attendant to the administration of norfenfluramine. Equally important, the amides of norfenfluramine affect the utilization of ingested food so as to decrease expectable weight gain. Thus, in addition to lowering cholesterol, the effects of anorexia and decreased food utilization combine to bring about reduction of weight gain without any apparent effect on the well-being of the subject and without more than mildly affecting the appetite and are, therefore, effective in controlling obesity in hypercholesteremia affected subjects. Metabolic studies show that the blood level of the norfenfluramine moiety of the fatty acid amides is small considering the amount of drug given.

The compounds of the present invention have the formula

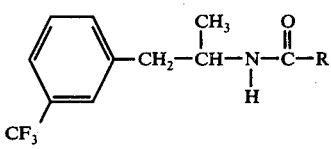

Formula I wherein R is selected from the group consisting of alkyl and alkenyl radicals having 12 to 22 carbon atoms.

In the preparation of the amides of norfenfluramine of this invention, any of the known processes for preparation of acid amides may be used, such as (1) Reaction of norfenfluramine in dry pyridine with phosphorus trihalide to form the phosphazo compound followed by reaction with the fatty acid or a mixture of fatty acids, which is the preferred method.

(2) Reaction of norfenfluramine with fatty acid halide or mixture of fatty acid halides;

(3) Reaction of fatty acid or mixture of fatty acids, norfenfluramine and suitable di-substituted carbodiimide;

(4) Reaction of fatty acid or mixture of fatty acids or mixture of fatty acids with norfenfluramine at 100°–300° C.;

(5) By catalytic dehydration of fatty acid or mixtures of fatty acids and norfenfluramine over a dehydrating agent such as sulfuric acid, p-phenolsulfonic acid and the like, or a cation exchange resin.

The acids used in the preparation of the amides of this invention may be of any origin, but usually the acids will originate from any of various natural fats and oils, specifically vegetable oils such as the tall oils, linseed oil, hempseed oil, safflower oil, soybean oil, sunflower oil, rice bran oil, corn oil, cottonseed oil, olive oil, peanut oil, palm oil, coconut oil, and animal oils which are found in most animal fats and fish oils.

It is therefore an object of the present invention to provide effective agents for reducing blood serum lipids and liver lipid levels in mammalian subjects, in particular cholesterol. Another object of the invention is to provide compositions and methods for lowering blood serum cholesterol in mammalian subjects for the purpose of combating hypercholesteremia and atherosclerosis. A still further object is to provide a method of combating obesity associated with atherosclerosis patients. Still other objects will become apparent to one skilled in the art from the description which follows and the appended claims.

DETAILED DESCRIPTION OF THE INVENTION

The present invention encompasses the novel fatty acid amides of norfenfluramine of Formula I as composition of matter and utilization of these amides primarily as cholesterol-lowering agents in combating atherosclerosis in mammalian subjects and secondarily in combating obesity.

The following chemical examples illustrate the preparation and establish physical constants of the preferred amides of Formula I.

EXAMPLE 1

(Linoleamide of Norfenfluramine)

N-[1-Methyl-2-(3-trifluoromethylphenyl)ethyl]octadeca-9,12-dienamide(cis-cis)

A mixture of 61.56 g. (0.18 mole) of norfenfluramine hydrochloride in chloroform was extracted with a 10% aqueous solution of sodium hydroxide. The chloroform layer was dried with sodium sulfate, filtered and concentrated in vacuo. The residue was dissolved in one liter of dry pyridine and 15.0 g. (0.11 mole) of phosphrous trichloride was added dropwise with ice bath cooling and stirring. After stirring at room temperature for one hour, 50.0 g. of pure linoleic acid (0.18 mole) was added. This solution was refluxed for 2 hours. Upon cooling, the solution was concentrated in vacuo. The residue was partitioned between chloroform and a 10% solution of sodium hydroxide. The chloroform layer was dried with sodium sulfate, filtered and concentrated in vacuo and distilled. B.P. 225°–230°/0.1 mm. Hg; Yield was 44.0 g. (0.09 mole); 50% of theory.

Analysis: Calculated for $C_{28}H_{42}F_3NO$: C, 72.23; H, 9.09; N, 3.01. Found: C, 72.37; H, 9.08; N, 2.97.

EXAMPLE 2

(Oleamide of Norfenfluramine)

N-[1-Methyl-2-(3-trifluoromethylphenyl)ethyl]octadec-9-enamide cis isomer

A mixture of 61.56 g. (0.18 mole) of norfenfluramine hydrochloride in chloroform was extracted with a 10% solution of sodium hydroxide. The chloroform layer was dried with sodium sulfate, filtered and concentrated in vacuo. The residue was dissolved in 1 liter of dry pyridine, and 15.0 g. (0.11 mole) of phosphorus trichloride was added dropwise while stirring, with ice bath cooling. After stirring at room temperature for 1 hour, 50.0 g. of pure oleic acid (0.18 mole) was added and the solution was refluxed for 15 hours. Upon cooling, the solution was concentrated in vacuo and the residue was partitioned between chloroform and a 10% solution of sodium hydroxide. The chloroform layer was dried over sodium sulfate, filtered and concentrated in vacuo. The residue was distilled. B.P. 230°–235°/0.1 mm. Hg. Yield was 42.0 g. (0.09 mole); 50% of theory.

Analysis: Calculated for $C_{28}H_{44}F_3NO$: C, 71.91; H, 9.48; N, 3.03. Found: C, 71.90; H, 9.43; N, 2.98.

EXAMPLE 3

(Elaidicamide of Norfenfluramine)

N-[1-Methyl-2-(3-trifluoromethylphenyl)ethyl]octadec-9-enamide trans isomer

Following the procedure of Example 2 but substituting 50.0 g. (0.18 mole) elaidic acid for the oleic acid, the titled compound was obtained in 15% yield. B.P. 230°–235°/0.1 mm Hg;

Analysis: Calculated for $C_{28}H_{44}F_3NO$: C, 71.91; H, 9.48; N, 3.00. Found: C, 71.83; H, 9.40; N, 2.99.

EXAMPLE 4

(Stearamide of Norfenfluramine)

N-[1-methyl-2-(3-trifluoromethylphenyl)ethyl]octadecanamide

Following the procedure of Example 2 but substituting 50.0 g. (0.18 mole) of stearic acid for oleic acid and recrystallizing the final concentrated residue from ethyl acetate rather than distilling it, the titled compound was obtained in 29% yield; m.p. 74°–76° C.

Analysis: Calculated for $C_{28}H_{46}F_3NO$: C, 71.61; H, 9.87; N, 2.98. Found: C, 71.61; H, 9.69; N, 2.90.

EXAMPLE 5

(Linoleamide of Norfenfluramine from Crude Linoleic Acid)

A mixture of 36.7 g (0.1 mole) of norfenfluramine hydrochloride in chloroform was extracted with a 10% aqueous solution of sodium hydroxide. The chloroform layer was dried with sodium sulfate, filtered and concentrated in vacuo. The residue was dissolved in 1 liter of dry pyridine, and 8.0 g (0.06 mole) of phosphorus trichloride was added dropwise with ice bath cooling and stirring. After stirring at room temperature for one hour, 14.0 g (0.05 mole) of linoleic acid containing in percentages by weight:

| | |
|---|---|
| linoleic acid | 65.5 |
| oleic acid | 19.0 |
| linolenic acid | 10.5 |
| palmitic acid | 3.5 |
| myristic acid | 0.5 |
| stearic acid | 0.5 |
| misc. fatty acids | 0.5 |
| | 100.0 | was added. This solution was refluxed for 2 hours. Upon cooling, the solution was concentrated in vacuo. The residue was partitioned between chloroform and a 10% solution of sodium hydroxide. The chloroform layer was dried with sodium sulfate, filtered, and concentrated in vacuo. The residue was dissolved in benzene and 75 ml portions were collected from a magnesium silicate column, eluated with benzene followed by a 10% solution of acetone and benzene. The portion containing the product was concentrated in vacuo and distilled. B.P. 220°0.05 mm; Yield 26% theory.

Analysis found: C,71.94; H,9.15; N,2.84.

Analysis using high pressure liquid chromatography showed that the product was a mixture of fatty acid amides of norfenfluramine and that the predominant amide by a wide margin was the linoleamide of norfenfluramine.

According to the method of the invention the compounds of this invention, the norfenfluramine amides of Formula I, are administered orally to mammalian subjects which are suffering from hypercholesteremia or atherosclerosis. The compounds may be administered orally in the form of capsules, tablets, syrups, elixirs, or as admixtures to food. When the compounds are administered as capsules, tablets, elixirs and syrups, they should be given generally at meal time in daily amounts of 50 to 600 mg/kg, preferably 200 to 600 mg/kg. When the compounds are administered as admixtures to food, the weight percentage of the compound based on food will vary from 0.025 to 0.5 weight % and preferably is 0.1 to 0.2 weight %. Generally, subjects under these dosage regimens will show favorable bias to reduction in weight gain and the subject will have a tendency to become less obese.

Pharmacology

Triton-induced Hyperlipidemia Tests

Fasted, male Sprague-Dawley rats weighing 250–350 g were fed ad libitum a commercial lab chow with free access to water. The animals were fasted overnight and administered Triton-WR-1339 (produced by Ruger Chemical Company, Inc., Irvington, New Jersey) as described by Schurr et al.; *Lipids* 7 68(1972) except the procedure was modified to use the saphenous vein and divided doses of 70 mg/kg. The rats were anesthetized with sodium pentobarbital and terminally bled by heart puncture. Serum was stored at −20° C. until it was analyzed for total cholesterol and triglycerides. Comparison was also made with clofibrate. As shown in Table 1, fatty acid amides of norfenfluramine reduced serum triglycerides and serum cholesterol.

Dietary-induced Hyperlipemia Tests

General feeding experiments were conducted on rats to determine the effect of the amides of this invention on serum and liver lipids of animals fed a basal diet and a basal diet supplemented with cholesterol. In addition, the effect of these drugs on serum lipoproteins was studied as well as their effect on body weight, gross feed efficiency, liver weight, appetite and energy utilization with respect to their metabolic size. Male, Sprague-Dawley rats weighing 150–175 g. were housed in cages with raised wire floors in a room kept at a temperature of 24°–26° C. with a 12-hour day and 12-hour night cycle, fed ad libitum a semipurified diet consisting by weight % composition: vitamin-free casein, 20; glucose, 63; hydrogenated coconut oil, 10; GBI Vitamin Fortification Mixture, Cat. #40060 obtained from General Biochemical Company of Chargrin Falls, Ohio, 1; modified salt mix of Williams and Briggs, Cat. #170911 obtained from General Biochemical Company, 4; and cellulose, 2; and watered. The modified salt mix provided the following amounts in grams of elements per Kg. of diet:

| | |
|---|---|
| calium | 7.1 |
| chlorine | 3.95 |
| copper | 0.0059 |
| iodine | 0.00067 |
| iron | 0.0287 |
| magnesium | 0.528 |
| manganese | 0.057 |
| phosphorus | 4.55 |
| potassium | 4.35 |
| sodium | 2.40 |
| sulfur | 0.73 |
| zinc | 0.135 |

The Vitamin Fortification Mix consisted of, in grams per Kg. of the mix:

| | |
|---|---|
| p-aminobenzoic acid | 11.0132 |
| ascorbic acid coated 97.5% pure | 101.6604 |
| biotin | 0.0441 |
| Vitamin $B_{12}$, 0.12% in mannitol | 2.9736 |
| calcium pantothenate | 6.6079 |
| choline dihydrogen citrate | 349.6916 |
| folic acid | 0.1982 |
| innositol | 11.0132 |
| menadione (Vitamin K) | 4.9559 |
| niacin | 9.9119 |
| pyridoxin HCl | 2.2026 |
| riboflavin | 2.2026 |
| thiamin HCl | 2.2026 |
| dry Vitamin A palmitate (500,000 units/g) | 3.9648 |
| dry Vitamin $D_2$ (500,000 units/g) | 0.4405 |
| dry Vitamin E acetate (500,000 units/g) | 24.2291 |
| balance, diluent corn starch | 466.6878 |

Diets were supplemented with 0.5% cholic acid, 1% cholesterol, and drug at the expense of glucose. The experimental period was 18–21 days with body weight and food measured at specified intervals. Animals were fasted overnight and terminally bled by cardiac puncture. Blood was anti-coagulated with ethylenediamine tetracetic acid and plasma was separated by centrifugation, and stored at −20° C. Livers were excised, weighed, and stored at −20° C. All samples remained at this temperature until they were analyzed for total lipids, total cholesterol, triglycerides and phospholipids. Gross feed efficiency together with the effect of metabolic size on food intake and the effect of drug on energy utilization were determined.

reduction in feed efficiency but in addition lowered serum and liver cholesterol was observed.

Similarly obtained data in Table 6 using the pure linoleamide of norfenfluramine of Example 1 also demonstrate the effect on serum and liver lipids.

In other analyses, increased dosage amounts of the mixed amides of Example 5 produced decreasing amounts of high density lipoproteins (HDL), and continuing lowered amounts of low density lipoproteins (LDL), Table 7.

Table 1

Effect of Fatty Acid Amides of Norfenfluramine on Serum Triglycerides and Cholesterol in Triton-Induced Hyperlipidemic Rats

| Test Group | Compound | Dose, mg/kg p.o | Serum Triglycerides mg/100 ml ± SD | % Change Triglycerides | Serum Cholesterol mg/100 ml ± SD | % Change Cholesterol |
|---|---|---|---|---|---|---|
| | None (control) | None | 588.2 ± 338.6 | 0 | 231.0 ± 59.9 | 0 |
| I | Clofibrate | 140 | 124.5 ± 7.8 | −79 | 173.0 ± 54.0 | −24.0 |
| | Linoleic Amide (Ex. 1) | 140 | 268.7 ± 69.6 | −54 | 209.0 ± 16.4 | − 9.5 |
| | None (control) | None | | | 123.5 ± 13.4 | 0 |
| II | Clofibrate | 140 | | | 94.1 ± 13.6 | −24 |
| | Linoleic & mixed acid amides (Ex. 5) | 140 | | | 101.9 ± 20.4 | −18 |
| | None (control) | None | 166.8 ± 82.0 | 0 | 140.0 ± 20.0 | 0 |
| | Clofibrate | 140 | 132.7 ± 64.5 | −20 | 109.3 ± 24.4 | −22 |
| III | Linoleic & mixed acid amides (Ex. 5) | 140 | 67.3 ± 19.1 | −60 | 109.0 ± 10.0 | −22 |
| | " | 70 | 64.3 ± 33.9 | −62 | 109.7 ± 16.6 | −22 |
| | " | 35[a] | 600.0 ± 214.7 | +260 | 189.0 ± 13.2 | +28 |
| | None (control) | None | 618.3 ± 302.2 | 0 | 281.5 ± 40.3 | 0 |
| | Clofibrate | 140 | 411.7 ± 118.0 | −34 | 213.0 ± 14.1 | −24 |
| IV | Oleic acid amide (Ex.2) of norfenfluramine | 140 | 166.3 ± 37.2 | −73 | 173.3 ± 10.2 | −39 |
| | Elaidic acid amide (Ex.3) of norfenfluramine | 140 | 260.0 ± 137.8 | −58 | 210.0 ± 47.8 | −25 |
| | Stearic acid amide (Ex.4) of norfenfluramine | 140 | 160.0 ± 110.0 | −74 | 214.3 ± 91.6 | −24 |

[a]anomalous result

Basal Diet

Results of testing the mixed amides of Example 5 and reference compounds in rats on a basal diet according to the foregoing procedure for dietary induced hyperlipemia are in Tables 2 and 3. Notably, the amides of this invention (Example 5) pronouncedly lowered food intake and feed efficiency, i.e., lower weight gain per unit of ingested food.

Basal Diet with Cholesterol

Results of testing the mixed amides of Example 5 an reference compounds in rats on a basal diet with added cholesterol according to the foregoing procedure for dietary induced hyperlipemia are in Tables 4 and 5. The mixed amides of Example 5 again produced pronounced Toxicity Comparison Motor activity of norfenfluramine and the amides of norfenfluramine of this invention were compared by determination of the activity in female, albino mice of the ICR strain by a modification of the method of Cook et al. in J. Pharmac. Exp. Ther. 113:11a (1955). Results suggest that the amides of norfenfluoramine have only mild effect on motor activity at 100 to 300 mg/kg, i.p. compared to strong effect noted for norfenfluramine at 6.5 mg/kg, i.p. No neurotoxicity was demonstrated for the amides of Example 5 in mice at dosages up to 300 mg/kg, i.p. and 1000 mg/kg, p.o., whereas tremors were observed with norfenfluramine at 40 mg/kg, i.p. and lethality at 100 mg/kg, i.p.

Table 2

Effect on Liver Weight, Body Weight and Food Consumption of Rats Fed a Basal Semi-purified Diet

| Treatment (c) | Dose[a] mg/kg/day | No. Rats | Liver wt, g ± S.D. Total | Liver wt, g ± S.D. per 100 g body wt. | Body wt, g ± S.D. Initial | Body wt, g ± S.D. Final | Food Consumed, g | Gross Feed Efficiency[b] |
|---|---|---|---|---|---|---|---|---|
| None | | 6 | 5.7 ± .3 | 2.7 ± .3 | 158 ± 18 | 212 ± 22 | 309 | .175 |
| Clofibrate .2% | 209 | 6 | 9.2 ± .4 | 4.4 ± .4 | 155 ± 16 | 210 ± 21 | 306 | .180 |
| Cholostyramine, 3% | 3120 | 6 | 5.8 ± .3 | 2.7 ± .3 | 151 ± 8 | 215 ± 13 | 316 | .203 |
| Amides of norfenfluramine (Ex. 5) | | | | | | | | |
| .1% | 96 | 4 | 5.3 ± .8 | 2.8 ± .2 | 176 ± 21 | 190 ± 28 | 241 | .058 |
| .2% | 204 | 6 | 7.0 ± .2 | 3.4 ± .7 | 171 ± 15 | 205 ± 22 | 304 | .112 |
| .5% | 490 | 4 | 5.9 ± .6 | 2.8 ± .1 | 185 ± 16 | 208 ± 24 | 276 | .083 |
| α-methylbenzyl-linoleamide .2% | | | | | | | | |

Table 2-continued
Effect on Liver Weight, Body Weight and Food Consumption of Rats Fed a Basal Semi-purified Diet

| Treatment (c) | Dose[a] mg/kg/day | No. Rats | Liver wt, g ± S.D. Total | per 100 g body wt. | Body wt, g ± S.D. Initial | Final | Food Consumed, g | Gross Feed Efficiency[b] |
|---|---|---|---|---|---|---|---|---|
| (d) | 182 | 6 | 6.7 ± .8 | 2.9 ± .3 | 158 ± 20 | 226 ± 30 | 331 | .210 |

[a]Based on percentage drug in diet and mean daily food consumed.
[b]Gross weight gain in grams/total food consumed in grams.
[c]Weight % of additive in food
[d]Prior art compound U.S. Pat. Nos. 3,621,043 and 3,728,459

Table 3
Effect on the Mean Concentration of Serum and Liver Lipids of Rats fed a Basal Semi-purified diet

| | Lipids | | | | | |
|---|---|---|---|---|---|---|
| | Serum mg/100 ml ± S.D. | | | Liver mg/g ± S.D. | | |
| Treatment (b) | Total | Cholesterol | Triglycerides | Total | Cholesterol | Triglycerides |
| None | 139.80 ± 22.57 | 69.67 ± 14.15 | 30.67 ± 2.89 | 46.86 ± 7.43 | 3.06 ± .18 | 4.39 ± 1.65 |
| Clofibrate,.2% | 143.70 ± 22.42 | 89.83 ± 8.77 | 31.83 ± 7.08 | 51.21 ± 7.89 | 2.63 ± .09 | 1.78 ± .43 |
| Cholestyramine 3.% | 116.60 ± 23.16 | 69.20 ± 10.55 | 25.80 ± 6.38 | 39.32 ± 5.95 | 2.87 ± .33 | 4.88 ± 2.54 |
| Amides of norfenfluramine (Ex. 5) | | | | | | |
| .1% | 153.30 ± 20.10 | 84.00 ± 10.58 | 35.33 ± 7.02 | 30.71 ± 2.88 | 3.55 ± .55 | 3.42 ± 2.60 |
| .2% | 191.00 ± 49.80 | 79.33 ± 10.39 | 75.33 ± 34.60 | 31.97 ± 2.49 | 3.22 ± .40 | 4.00 ± 2.10 |
| .5% | 175.50 ± 9.40 | 86.00 ± 14.99 | 70.00 ± 17.51 | 34.51 ± 4.06 | 4.10 ± .27 | 6.82 ± .46 |
| α-methylbenzyl-linoleamide (a) | | | | | | |
| .2% | 199.80 ± 60.9 | 77.50 ± 3.91 | 72.33 ± 29.92 | 40.05 ± 11.37 | 3.34 ± .24 | 4.85 ± 2.71 |

(a) Prior art compound U.S. Pat. Nos. 3,621,032 and 3,728,459
(b) Weight % of additive in food

Table 4
Effect on Food Consumption and Feed Efficiency of Rats Fed a Basal Semi-purified Diet Supplemented with Cholesterol

| Treatment[d] | No. Rats | Dose[a] mg/kg/day | Liver wt, g ± S.D. Total | Per 100 g body wt. | Body wt, g ± S.D. Initial | Final | Food Consumed, g | Gross Feed Efficiency[b] |
|---|---|---|---|---|---|---|---|---|
| None | 6 | | 7.5 ± .6 | 3.6 ± 2 | 132 ± 4 | 208 ± 13 | 321 | .237 |
| Clofibrate, .2% | 6 | 198 | 10.4 ± 2.6 | 4.9 ± 1.2 | 135 ± 5 | 208 ± 16 | 340 | .215 |
| Cholestyramine, 3% | 6 | 2930 | 6.1 ± .5 | 2.9 ± .2 | 132 ± 13 | 208 ± 18 | 336 | .226 |
| Amides of norfenfluramine (Ex. 5) | | | | | | | | |
| .1% | 6 | 91 | 5.9 ± .5 | 3.4 ± .2 | 138 ± 6 | 177 ± 15 | 288 | .135 |
| .2% | 6 | 194 | 6.1 ± .3 | 3.2 ± .1 | 148 ± 9 | 190 ± 7 | 328 | .128 |
| .5% | 6 | 466 | 5.7 ± .4 | 3.3 ± .1 | 148 ± 12 | 172 ± 11 | 298 | .081 |
| α-methylbenzyl-linoleamide[c] | | | | | | | | |
| .2% | 4 | 199 | 7.1 ± 1.3 | 3.7 ± .2 | 137 ± 8 | 192 ± 25 | 311 | .177 |

[a]Based on percentage drug in diet and mean daily food consumed.
[b]Gross weight gain in gross/total food consumed in grams.
[c]Prior art compound U.S. pat. nos. 3,621,043 and 3,728,459
[d]Weight % of additive in food.

Table 5
Effect on Serum and Liver Lipids of Rats Fed a Basal Semi-purified Diet Supplemented with Cholesterol

| | Lipids | | | | | |
|---|---|---|---|---|---|---|
| | Serum, mg/100 ml ± S.D. | | | Liver, mg/g ± S.D. | | |
| Treatment[b] | Total | Cholesterol | Triglycerides | Total | Cholesterol | Triglycerides |
| None | 635.67 ± 73.03 | 272.67 ± 44.19 | 253.83 ± 67.69 | 120.00 ± 23.22 | 25.37 ± 6.51 | 12.45 ± 10.10 |
| Clofibrate,.2% | 430.33 ± 119.37[a] | 235.00 ± 68.27 | 126.50 ± 47.21[a] | 93.83 ± 12.06[a] | 14.17 ± 9.10[a] | 7.83 ± 2.22 |
| Cholestyramine, 3% | 242.83 ± 70.05[a] | 93.67 ± 17.50[a] | 180.00 ± 82.19 | 76.67 ± 8.09[a] | 6.15 ± 1.37[a] | 11.13 ± 4.11 |
| Amides of norfenfluramine (Ex.5) | | | | | | |
| .1% | 375.67 ± 69.11[a] | 166.17 ± 44.58[a] | 176.00 ± 33.92[a] | 83.83 ± 7.96[a] | 4.80 ± 3.42[a] | 7.33 ± .79 |
| .2% | 266.33 ± 40.27[a] | 141.33 ± 28.08[a] | 184.67 ± 44.59 | 78.83 ± 12.83[a] | 2.55 ± 2.65[a] | 6.50 ± .97 |
| .5% | 286.67 ± 58.03[a] | 163.00 ± 23.24[a] | 299.50 ± 51.88 | 75.33 ± 12.94[a] | 1.50 ± .50[a] | 7.07 ± .86 |
| α-methylbenzyl-linoleamide[b] | | | | | | |

Table 5-continued
Effect on Serum and Liver Lipids of Rats
Fed a Basal Semi-purified Diet Supplemented with Cholesterol

| Treatment[b] | Lipids | | | | | |
|---|---|---|---|---|---|---|
| | Serum, mg/100 ml ± S.D. | | | Liver, mg/g ± S.D. | | |
| | Total | Cholesterol | Triglycerides | Total | Cholesterol | Triglycerides |
| .2% | 453.25 ± 90.58[a] | 197.75 ± 23.24 | 262.50 ± 51.88 | 84.00 ± 14.26[a] | 8.33 ± 1.37[a] | 4.35 ± 2.88 |

[a] $p<.05$ by Student t-test.
[b] Prior art compound U.S. Pat. Nos. 3,621,043 and 3,728,459
[c] Weight % of additive in food.

Table 6
Effect on Linoleamide of Norfenfluramine on
Serum and Liver Lipids in Rats Fed a
Hypercholesteremic Diet (a)(b)

| Treatment (d) | Serum Lipids mg/100 ml. | | | Liver Lipids mg/g | | |
|---|---|---|---|---|---|---|
| | Cholesterol | Trigly-cerides | Phospho-lipids | Cholesterol | Trigly-cerides | Phospho-Lipids |
| None | 454 ± 121 | 105 ± 37 | 97.5 ± 32.6 | 57.32 ± 4.06 | 30.69 ± 14.66 | 23.98 ± 5.44 |
| Linoleaamide of norfenfluramine (Ex. 1) 0.2% | 212 (c) ± 30 | 156(c) ± 62 | 105.4 ± 18.4 | 7.15(c) ± 0.73 | 5.59(c) ± 3.67 | 24.1 + 8.75 |

(a) ± values are standard deviation of 10 animals per group.
(b) Semi-purified diet supplemented with 1% cholesterol and 0.5% cholic acid at expense of glucose.
(c) $p<.05$ as determined by Student's t-test.
(d) Weight % of additive in food.

Table 7
Effect on Serum Lipoproteins of Rats
Fed a Semi-purified Diet Supplemented with Cholesterol

| Treatment[c] | No. bands | Percentage Composition[a] | | | |
|---|---|---|---|---|---|
| | | VLDL | LDL | HDL | Albumin |
| None | 6 | 37.58 | 45.94 | 2.52 | 13.93 |
| Clofibrate, .2% | 8 | 25.76 | 42.56 | 9.03 | 22.63 |
| Cholestyramine, 3% | 7 | 17.00 | 35.07 | 16.15 | 31.77 |
| Linoleamide of norfenfluramine (Ex. 5) | | | | | |
| .1% | 6 | 36.92 | 11.29 | 20.07 | 31.69 |
| .2% | 6 | 23.65 | 15.42 | 12.11 | 42.81 |
| .5% | 4 | 35.78 | 16.98 | 2.76 | 40.46 |
| α-methylbenzyl-linoleamide, .2%[b] | 7 | 36.19 | 18.51 | 29.62 | 15.65 |

[a] VLDL, very low density lipoproteins; LDL, low density lipoproteins; and HDL, high density lipoproteins as determined on a Beckman-Gilford spectrophotometer.
[b] Prior art compound U.S. Pats. 3,621,043 and 3,728,459.
[c] Weight % of additive in food.

The $LD_{50}$ of the amides of norfenfluramine determined by a method adapted from Finney Statistical Methods in Biological Assay, Hafner Pub. Co., New York, 2nd Ed. (1964), was found to be greater than 10,000 mg/kg, p.o. The $KD_{50}$ of norfenfluramine by the same method was 137 mg/kg. The therapeutic index of the amides of norfenfluramine appeared very favorable compared to norfenfluramine and no adverse reactions of the amides on serum glucose, microsomal enzymes or monoamine oxidase were observed.

Synthesis of β Sterol and Nonsaponifiable Substances

The effect of the mixed amides of Example 5 and reference compounds on β Sterol synthesis was determined by a modified procedure of Hill and Dvornik Arch. Biochem. Biophys. 114 (1966), 88. Male Sprague-Dawley rates weighing 127–175 g. were freely provided a basal semi-purified diet and water. The rats were housed in cages with raised wire floors in a room kept at a temperature of 24°–26° C. with a 12-hour day-12-hour night cycle. The cycle was reversed so the night cycle corresponded to the working day to take advantage of the circadian rhythm that favors cholesterol synthesis. The test period was five days and 20 μCi sodium acetate-1-$^{14}$C (Sp. act. 56 mCi/m mole) administered intraperitoneally. Animals were sacrificed under carbon dioxide and the distal 10 cm of the ileum as well as the median and left liver lobes excised and homogenized. Subsequently, the β Sterols were isolated as the digitonide and the radioactivity determined in a Packard Tricarb Liquid Scintillation Spectrometer Model 3385 using 0.5% 2,5 diphenyloxazole and 8% naphthalene in a solvent mixture of 40% toluene, 40% dioxane and 20% absolute ethanol. Data for the effect of the mixed amides of Example 5 on the synthesis of nonsaponifiable substances and β Sterols as determined by the Digitonide method are shown in Table 8. Results indicate that at doses of 140 mg/kg, p.o. the amides of this invention reduced sterol synthesis from control values by 48% in the liver and 15% in the ileum. A prior art compound, α-methylbenzyllinoleamide at 140 mg/kg, p.o. had no effect on cholesterol synthesis in either tissue.

Table 8
β-Sterol Synthesis. Incorporation of
Acetate-1-$^{14}$C Into Nonsaponifiable and
Digitonin Precipitate Sterols

| Compound | No. rats | Dose mg/kg p.o. | Tissue | Acetate-1-$^{14}$C incorporated n moles/g tissue ± S.D. | |
|---|---|---|---|---|---|
| | | | | Non-saponifiable | Digitonide |
| None | 15 | | Liver | 4.123 ± 1.718 | 3.028 ± 1.072 |
| | 15 | | Ileum | 7.841 ± 2.467 | 6.752 ± 1.248 |
| Clofibrate | 10 | 140 | Liver | 2.943 ± 1.707 | 1.588 ± 1.216 |

Table 8-continued

| Compound | No. rats | Dose mg/kg p.o. | Tissue | β-Sterol Synthesis. Incorporation of Acetate-1-$^{14}$C Into Nonsaponifiable and Digitonin Precipitate Sterols Acetate-1-$^{14}$C incorporated n moles/g tissue ± S.D. | |
|---|---|---|---|---|---|
| | | | | Non-saponifiable | Digitonide |
| Cholestyramine | 10 10 | 660 | Ileum Liver Ileum | 6.774 ± 1.447 14.869 ± 4.027 13.533 ± 3.904 | 6.098 ± .909 15.456 ± 2.710 12.085 ± 1.430 |
| Linoleic and mixed acid amides (Ex.5) of norfenfluramine | 4 4 | 140 | Liver Ileum | 2.077 ± 1.246 7.022 ± 2.125 | 1.581 ± 1.158 5.731 ± 1.499 |
| α-methylbenzyl linoleamide, (a) | 4 4 | 140 | Liver Ileum | 4.533 ± 3.131 7.648 ± 1.664 | 3.882 ± 2.887 5.947 ± .654 |

(a) prior art compound U.S. patents 3,621,043 and 3,728,459

Formulation and Administration

The cholesterol-lowering anti-obesity agents of this invention may be orally administered, usually the amount administered is 0.5 to 10 g, per day, preferably 0.25 to 2.5 g per day and the administration may be continued for several months. The cholesterol-lowering agent may be in any suitable form which is conventional for oral administration. Thus, it may be encased in a capsule, or it may be in liquid form such as a slurry, in a tablet form or in a powder form. In preparing the agents in these various forms, the active compound may be mixed with a liquid carrier such as an edible oil. Mixtures of two or more of the agents of this invention may be used in any of the foregoing described dosage forms.

Tablet Preparation

A granulation is prepared of

| | Parts by wt. |
|---|---|
| Lactose | 74 |
| Starch | 26 |
| Water sufficient to granulate | |

The granulation is dried and screened.

| | Parts by wt. |
|---|---|
| Amide of norfenfluramine (structural Formula I) | 100 |
| Lactose granulation above | 145 |
| Magnesium stearate | 5 | are mixed together and compressed into tablets weighing 250 mg and containing 100 g of the active ingredient per dose unit.

Slurry Dosage Form

An elixir is prepared containing per liter

| Linoleamide of norfenfluramine (structural Formula I) | 10.0 g |
|---|---|
| Ethyl alcohol | 150.0 ml |
| Glycerin | 350.0 ml |
| Sorbitol (70% solution) | 350.0 ml |
| Benzoic acid | 1.0 g |
| Sodium saccharin | 0.3 g |
| Coloring agent (FD and C Red No. 2) | 0.02 g |
| Imitation raspberry flavor | 0.2 ml |
| Spice vanilla | 0.02 ml |
| Distilled water | q.s. to 1,000 ml |

The active ingredient of Formula I is added to about two-thirds of the ethanol and all of the glycerin and sorbitol are added and the mixture thoroughly triturated. The saccharin and coloring agent are dissolved in a small amount of the water and coloring agent dissolved therein. The aqueous solution is then added to the alcohol solution and the balance of the water is added to bring the volume to 1 liter and after mixing and filtering an elixir is obtained containing 10 mg of the active ingredient per ml. A unit dose of 15 ml (1 tablespoon) thus contains 150 mg of active ingredient.

Any of the linoleamides of this invention or a mixture thereof may be used to prepare either the tableted form or the elixir form. The active ingredient can be suitably varied within the range of 50 to 400 mg and preferably 50 to 200 mg per dosage unit. In addition, other therapeutic agents may be added to these formulations if desired.

Powders are prepared with various conditioners added, such as starches, gums, etc., for mixing with human or animal food.

Various changes and modifications in the procedures for preparing these hypocholesteremic amides of norfenfluramine and incorporating the same into therapeutic compositions will occur to those skilled in the art, and to the extent that such changes and modifications are embraced by the appended claims, it is to be understood that they constitute part of this invention.

What is claimed is:

1. A fatty acid amide of norfenfluramine having effective cholesterol-lowering activity in mammals of the formula:

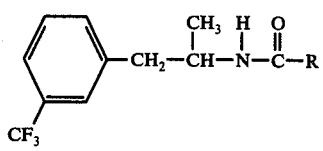

wherein R is selected from the group consisting of alkyl having 12 to 22 carbon atoms and alkenyl having 12 to 22 carbon atoms.

2. A compound of claim 1 which is N-[1-methyl-2-(3-trifluoromethylphenyl)-ethyl]octadeca-9,12-dienamide cis-cis isomer.

3. A compound of claim 1 which is N-[1-methyl-2(3-trifluoromethylphenyl)ethyl]octadec-9-enamide cis isomer.

4. A compound of claim 1 which is N-[1-methyl-2-(3-trifluoromethyl-phenyl)ethyl]octadec-9-enamide trans isomer.

5. A compound of claim 1 which is N-[1-methyl-2-(3-trifluoromethyl-phenyl)ethyl]]octadecanamide.

6. A mixture of fatty acid amides of norfenfluramine having effective cholesterol-lowering activity in mammals wherein the amides have the formula:

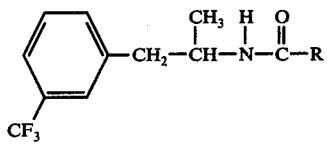

and wherein R is selected from the group consisting of alkyl having 12 to 22 carbon atoms and alkenyl having 12 to 22 carbon atoms.

7. A mixture of claim 6 wherein the predominant fatty acid amide is the linoleamide of norfenfluramine.

8. A method of combating atherosclerosis in a mammal, which consists of administering orally to a mammal in need thereof a compound or a mixture of compounds having the formula:

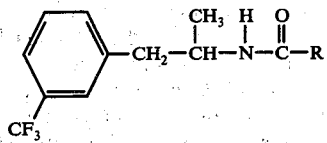

wherein R is selected from the group consisting of alkyl having 12 to 22 carbon atoms and alkenyl having 12 to 22 carbon atoms.

9. A method of claim 8 wherein the compound is N-[1-methyl-2-(3-trifluoromethylphenyl)ethyl]octadeca-9,12 dienamide cis-cis isomer.

10. A method of claim 8 wherein the compound is N-[1-methyl-2(3-trifluoromethylphenyl)ethyl]]octadec-9-enamide cis isomer.

11. A method of claim 8 wherein the compound is N-[1-methyl-2-(3-trifluoromethylphenyl)ethyl]octadec-9-enamide trans isomer.

12. A method of claim 8 wherein the compound is N-[1-methyl-2-(3-trifluoromethylphenyl)ethyl]octadecanamide.

13. A method for combating atherosclerosis and obesity in a mammal in need thereof which consists of administering to a mammal in need thereof a compound or a mixture of compounds having the formula:

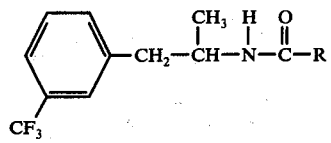

wherein R is selected from the group consisting of alkyl having 12 to 22 carbon atoms and alkenyl having 12 to 22 carbon atoms.

14. A method of claim 13 wherein the compound is N-[1-methyl-2-(3-trifluoromethylphenyl)-ethyl]octadeca-9,12 dienamide cis-cis isomer.

15. A pharmaceutical composition for combating atherosclerosis, in unit dosage form comprising, (a) an effective amount of a fatty acid amide of norfenfluramine or mixtures thereof having the formula:

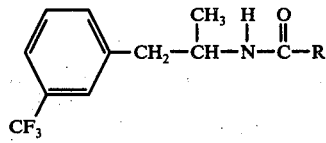

wherein R is selected from the group consisting of alkyl having 12 to 22 carbon atoms and alkenyl having 12 to 22 carbon atoms, and (b) a pharmaceutical carrier therefor.

16. A pharmaceutical composition of claim 15 wherein the fatty acid amide of norfenfluramine is N-[1-methyl-2-(3-trifluoromethylphenyl)-ethyl]octadeca-9,12-dienamide cis-cis isomer.

17. A pharmaceutical composition of claim 15 wherein the fatty acid amide of norfenfluramine is N-[1-methyl-2(3-trifluoromethylphenyl)ethyl]octadec-9-enamide cis isomer.

18. A pharmaceutical composition of claim 15 wherein the fatty acid amide of norfenfluramine is N-[1-methyl-2-(3-trifluoromethylphenyl)ethyl]octadec-9-enamide trans isomer.

19. A pharmaceutical composition of claim 15 wherein the fatty acid amide of norfenfluramine is N-[1-methyl-2(3-trifluoromethylphenyl)ethyl]octadecanamide.

20. A pharmaceutical composition of claim 15 wherein the fatty acid amides of norfenfluramine are present as a mixture.

21. A pharmaceutical composition of claim 20 wherein the fatty acid amide of norfenfluramine predominating in the mixture is N-[1-methyl2-(3-trifluoromethylphenyl)ethyl]octadec-9,12-dienamide cis-cis isomer.

* * * * *